United States Patent
Thommen et al.

(10) Patent No.: US 8,052,634 B2
(45) Date of Patent: Nov. 8, 2011

(54) BREAST SHIELD

(75) Inventors: Daniel Thommen, Steinhausen (CH); Simon Furrer, Lucerne (CH); Michael Larsson, Zug (CH)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 12/097,003

(22) PCT Filed: Dec. 21, 2006

(86) PCT No.: PCT/CH2006/000718
§ 371 (c)(1),
(2), (4) Date: Jun. 11, 2008

(87) PCT Pub. No.: WO2007/071093
PCT Pub. Date: Jun. 28, 2007

(65) Prior Publication Data
US 2008/0312586 A1 Dec. 18, 2008

(30) Foreign Application Priority Data
Dec. 22, 2005 (CH) .................................... 2045/05

(51) Int. Cl.
*A61M 1/06* (2006.01)
(52) U.S. Cl. .......................................... 604/74; 604/114
(58) Field of Classification Search ............... 604/74–76, 604/346, 385.07, 113–114
See application file for complete search history.

(56) References Cited

U.S. PATENT DOCUMENTS

| 4,052,981 | A | * | 10/1977 | Bachmann ........................ 601/71 |
| 4,074,222 | A | * | 2/1978 | Kiyokawa et al. ............. 338/212 |
| 4,929,229 | A | * | 5/1990 | Larsson .......................... 604/74 |
| 5,897,580 | A | * | 4/1999 | Silver ............................ 607/108 |
| 6,172,344 | B1 | * | 1/2001 | Gordon et al. .................. 219/529 |
| 6,358,226 | B1 | * | 3/2002 | Ryan ................................ 604/74 |
| 2002/0019654 | A1 | * | 2/2002 | Ellis et al. ..................... 607/98 |
| 2003/0073951 | A1 | | 4/2003 | Morton et al. |
| 2003/0121899 | A1 | | 7/2003 | Argersinger et al. |
| 2003/0191432 | A1 | | 10/2003 | Silver |
| 2004/0087898 | A1 | * | 5/2004 | Weniger ........................ 604/74 |
| 2006/0035081 | A1 | * | 2/2006 | Morita et al. ................. 428/408 |

FOREIGN PATENT DOCUMENTS

| WO | 00/47247 | | 8/2000 |
| WO | 01/95841 | A2 | 12/2001 |
| WO | 2005/070476 | A2 | 8/2005 |

* cited by examiner

*Primary Examiner* — Theodore Stigell
(74) *Attorney, Agent, or Firm* — McDonnell Boehnen Hulbert & Berghoff LLP

(57) ABSTRACT

A breast cup (4) for use with a breast pump (1) for pumping off breast milk comprises a breast-cup funnel (40) for application to a breast, a first coupling part (42) for connection to the breast pump (1), and a second coupling part (43) for connection to a milk collection vessel (44). The breast cup (4) has an electrical resistance heating element (5) that warms it and that is made of an electrically conductive plastic material.

15 Claims, 4 Drawing Sheets

BREAST SHIELD

TECHNICAL FIELD

The invention relates to a breast shield.

PRIOR ART

Breastpumps for expressing human breastmilk are well known. They usually comprise a vacuum pump, one or two breast shields that can be connected thereto and that can be placed on the mother's breast or on both breasts, and a milk collection container that can be connected to each breast shield and collects the expressed breastmilk.

It is also known that applying heat to the breast before and during the pumping procedure not only increases the comfort experienced by the mother, but also widens the milk ducts, helps release blockages and makes the areola softer.

Thus, U.S. Pat. No. 5,897,580 discloses a C-shaped breast-shield insert with a chemical filling that can undergo an exothermic reaction. WO 2005/070476 discloses an electrically heatable breast-shield insert, in which the electrical resistance heating wires are arranged either in the breast-shield insert itself or in the breast-shield funnel.

US 2002/0198489 discloses a breast shield with a twin-walled breast-shield funnel. A fluid, for example warm water, can be conveyed through the space between the walls, in order to warm the breast shield. U.S. Pat. No. 6,358,226 proposes pumping warm air into a twin-walled breast shield.

US 2004/0087898 describes a breast shield with an electrical resistance heating wire which is either arranged on the outer or inner surface of the breast shield or is embedded in its material.

Heatable breast-shield inserts have the disadvantage that the mother has to fit another separate part on the breast-shield set before she can begin expressing milk. This is undesirable at night or when she is pressed for time. Breast shields with electrical resistance heating wires are complicated to produce. It is difficult, in particular, to inlay wires and to encapsulate them by injection molding. Moreover, there is a danger of the wires being able to come loose from the breast shield if the latter is used incorrectly. The sight of the wires can also be off-putting to the mother, since she is conscious of applying electrical current to the breast. Moreover, the heating coils block the mother's view of the nipple and the surrounding area, making it difficult for her to observe the pumping procedure.

DISCLOSURE OF THE INVENTION

An object of the invention is therefore to make available an alternative device for warming the mother's breast, which can be used before and during pumping.

This object is achieved by a breast shield with the features of patent claim 1.

The breast shield according to the invention for use with a breastpump for expressing breastmilk comprises a breast-shield funnel for application to a mother's breast, a first coupling part for connection to the breastpump, and a second coupling part for connection to a milk collection container. The breast shield also has an electrical resistance heating element for warming it, said electrical resistance heating element being made of an electrically conductive plastic material.

In a preferred embodiment, the electrically conductive plastic material is a plastic base material and comprises an electrically conductive additive. The breast shield is preferably produced in a two-component or multi-component injection-molding operation.

The breast shield according to the invention has the advantage that it does not require an insert that has to be heated. In addition, the breast-shield funnel can also be made relatively narrow, since no chamber is needed to receive a heating medium. By virtue of the two-component or multi-component injection-molding operation, the resistance heating element is connected practically unreleasably to the rest of the breast shield, such that it does not suffer damage even when subjected to considerable stress. Another advantage is that the resistance heating element is easier to work onto or into the material of the breast shield, such that its placement on the breast shield and also its configuration are more flexible and afford a greater range of options. Furthermore, the resistance heating element can be configured such that it is does not at first sight look as if it conducts current.

Further advantageous embodiments are set forth in the dependent patent claims.

BRIEF DESCRIPTION OF THE DRAWINGS

The subject matter of the invention is explained below on the basis of preferred illustrative embodiments depicted in the attached drawings, in which.

EMBODIMENTS OF THE INVENTION

Figure 1:
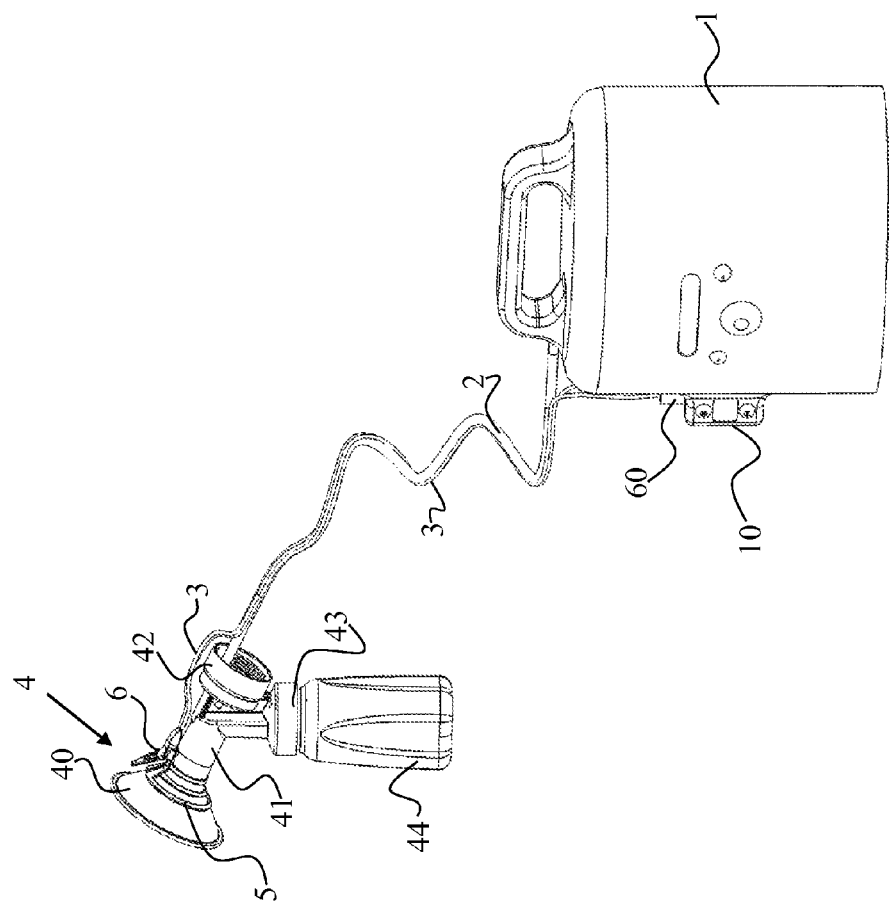
FIG. 1 shows a perspective view of a breastpump set with breastpump and breast shield according to the invention, in a first embodiment.

FIG. 1 shows a breastpump set in the state when assembled and ready for use. The breastpump set comprises a breastpump 1 in the form of a motor-driven vacuum pump or suction pump arranged in a housing, one or more breast shields 4, a milk collection container 44 that can be connected to each breast shield, and a suction line 2 for connecting the breastpump 1 to the corresponding breast shield 4.

The breastpump set shown is just one illustrative embodiment from a large number of possible examples. Instead of the motor-driven vacuum pump, it can also comprise a manual pump which is connected to the breast shield via a suction line or directly. The form of the breast shield can also vary. All suitable containers or bags are suitable as the milk collection container.

The breast shield 4 preferably has a breast-shield funnel 40, which is placed on the breast in such a way that it surrounds the nipple but leaves the latter free. The breast-shield funnel 40 is followed by a breast-shield neck 41, which ends in a first coupling part 42. A second coupling part 43 branches off from the breast-shield neck 41 at an angle thereto. The first coupling part 42 serves for connection of the suction line 2. In the example shown here, a manual pump or a small motor-driven vacuum pump, in particular a battery-driven vacuum pump, can alternatively be attached, for example screwed on. The milk collection container 44 in the form of a bottle can be screwed onto the second coupling part 43. Alternatively, a milk collection bag can also be secured. In the example shown here, the breast shield is formed in one piece and is preferably made of a rigid plastic material, in particular of polypropylene (PP).

The breast shield 4 is provided with an electrical resistance heating element 5. This electrical resistance heating element 5 is preferably arranged in the area of the breast-shield funnel 40. However, it can also be arranged on the neck or, depending on the shape of the breast shield 4, at another location, as long as it can deliver sufficient warmth to the area of the breast-shield funnel 40. The resistance heating element 5 preferably runs in a spiral shape or, as is shown here, in concentric circles on the breast-shield funnel 40. However, other configurations of the resistance heating element are also possible. It can be arranged, as is shown here, on the outer surface of the breast shield 4. However, it can likewise be arranged on the inner surface or be embedded in the material of the breast shield 4. An electrical line 3 leading to the breastpump 1 is provided for activating the resistance heating element 4. This electrical line 3 is preferably connected to the suction line 2 and divides only in the end areas of the line. That is to say, the electrical line 3 has its own electrical connection or its own first contact element 6 in the area of the breast-shield funnel 40 and its own second contact element 60 on the housing of the breastpump 1. These are preferably plug-in connections. In the example shown here, the electrical module for controlling the heating or the resistance heating element 5 is a module 10 mounted externally on the main housing of the breastpump 1. However, it can of course also be integrated into the main housing of the breastpump, and the corresponding operating buttons, keys or panels can be arranged on the main housing.

Figure 2A:
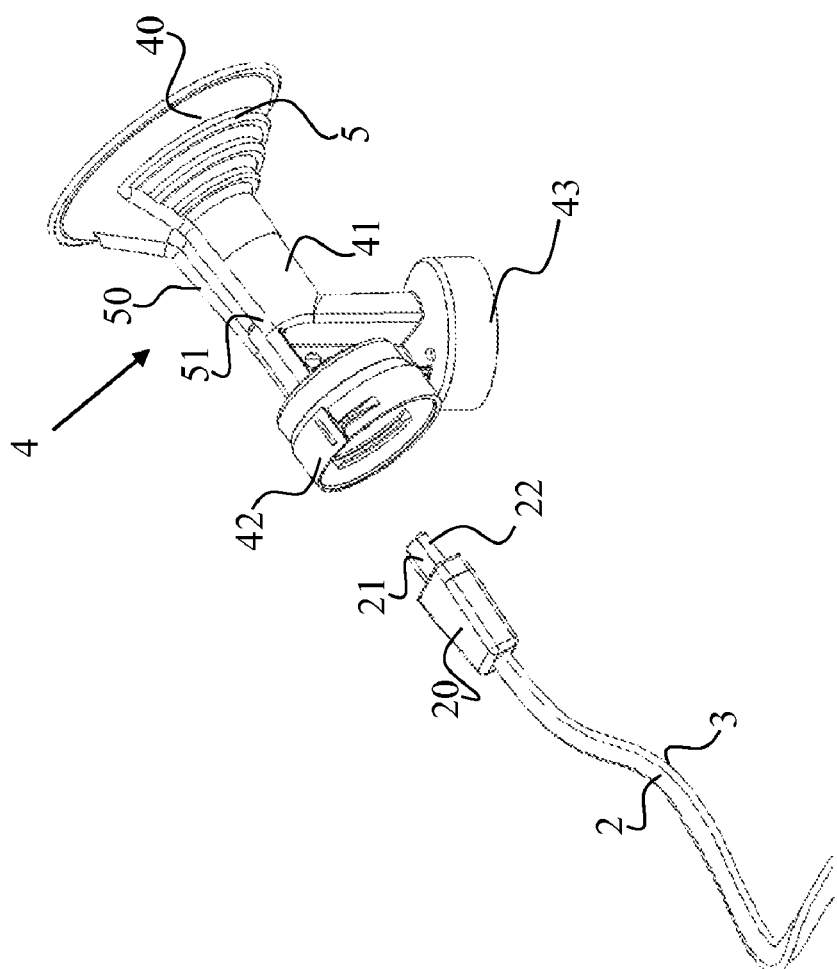
FIG. 2a shows a perspective view of a breast shield according to the invention, in a second embodiment.
Figure 2B:
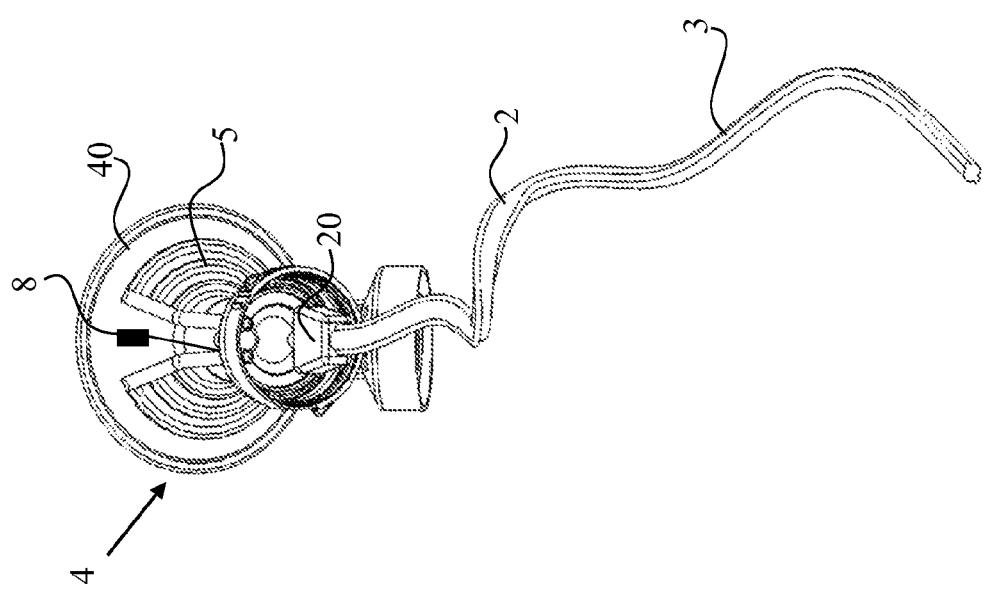
FIG. 2b shows another perspective view of the breast shield according to FIG. 2a, and FIG. 3 shows a perspective view of a two-part breast-shield funnel according to a third embodiment of the invention.

FIGS. 2a and 2b show another embodiment. Here, a common plug 20 is present for the suction line 2 and the electrical line 3, such that, in the first coupling part 42, the electrical connection 22 is arranged adjacent to the connection 21 of the suction line 2. Correspondingly, connection lines 50, 51 are present on the breast shield 4 and connect the electrical connection 22 to the resistance heating element 5.

Figure 3:
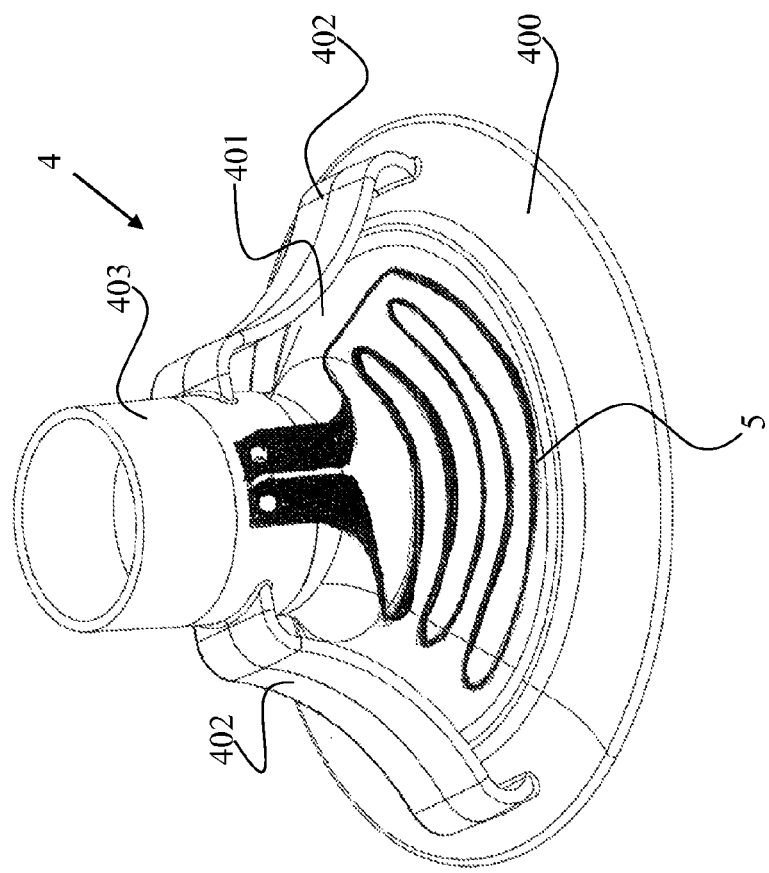

FIG. 3 shows another embodiment, with only the breast-shield funnel 40 being shown. Here, the breast shield 4 is not formed in one piece as in the previous examples, but in more than one piece. The breast-shield funnel 40 is designed as an insert element that can be inserted into the breast-shield neck. For this purpose, the breast-shield funnel 40 itself has a short neck 403. The breast-shield funnel 40 has a rigid front area 400, i.e. lying closest to the mother, a soft middle area 401, and the rigid neck 403. Neck 403 and front area 400 are fixed to each other via rigid webs 402. Breast shields of this kind are known. Their advantage is that the middle area shapes itself optimally to the mother's breast. The rigid area 400 is usually made of polypropylene (PP), and the soft area 401 of a thermoplastic elastomer (TPE), for example Thermolast K. The novel feature now is that the resistance heating element 5 is arranged in the soft middle area 401. Of course, the breast-shield neck 41 and the coupling parts 42, 43 can also be connected in one piece to the rigid neck 403 of the breast-shield funnel 40.

In all of the examples mentioned above, the electrical resistance heating element 5 for warming the breast is now made of an electrically conductive plastic material, that is to say of a plastic which is either electrically conductive itself or which has been made electrically conductive by means of additives.

Baytron P is suitable as a plastic that is electrically conductive itself.

If the plastic has been made electrically conductive, then it has a plastic base material and an electrically conductive additive. The plastic base material is preferably, but not exclusively, polyamide (PA), polypropylene (PP) or polyethylene (PE).

The additive is preferably fibrous. If fibers are used, they preferably have a length of 100 to 300 µm. Particularly suitable fibers are carbon fibers, copper fibers and iron fibers. The additive can be composed of a single type of these fibers or of a mixture of these.

Good results have been achieved with plastics from Albis (ALCOM PA66 910/1 CF10, ALCOM PA66 910/1 CF30), with plastics from General Electrics Plastics (PTC-B and PTC-B1) and with polypropylene from Borealis, type BH 345 MO+ (with 20% carbon fibers).

The fibrous additive is preferably admixed to the plastic base material in a quantity of 10% to 30% (percent by weight). The advantage of the fibrous additives is that when the base material is heated, they maintain their link to one another and, consequently, do not lose their electrical conductivity.

However, the additive can also be in powder form. Iron powder, copper powder and soot are particularly suitable. Here too, the powders can be used individually or mixed. The powder preferably has a particle size of 100 nm to 1 µm.

The powdery additive is preferably admixed to the plastic base material in a quantity of 80% to 90% (percent by weight).

Materials are preferably used that have a specific resistance of ca. 2,500 $\Omega mm^2/m$. The breast shield according to the invention then has a resistance of ca. 20$\Omega$.

The breast shield with the resistance heating element is preferably produced in a two-component or multi-component injection-molding operation. Production operations of this kind are well known and are therefore not discussed in detail here. In the two-component or multi-component injection-molding operation, after the first component has hardened in the injection-molding die, the cavity is enlarged and a second component or further components are added using a second injection-molding unit. The enlargement can be effected either by slides or by changing the cavity by means of a rotary tool or rotary table. One component is in this case the base material of the breast shield, and a second component is the resistance heating element. Further components can be used depending on the requirements.

In a preferred embodiment, the breast shield is further equipped with at least one sensor for monitoring the temperature. In the event of overheating, this sensor can trigger an alarm or deliver a signal to a control device of the heating element, in order to keep the temperature to a constant value or a constant range of values. A suitable temperature sensor is designated by reference number 8 in FIG. 2b.

LIST OF REFERENCE NUMBERS 1 breastpump
10 module
2 suction line
20 plug
21 suction line connection
22 electrical connection
3 electrical line
4 breast shield
40 breast-shield funnel
41 breast-shield neck
42 first coupling part
43 second coupling part
44 milk collection container
400 rigid front area

401 soft middle area
402 web
403 rigid neck
5 resistance heating element
6 first contact element
60 second contact element
7 plug
8 temperature sensor

The invention claimed is:

1. A breast shield for use with a breastpump for expressing breastmilk, the breast shield comprising:
   a breast shield funnel for application to a mother's breast;
   a first coupling part for connection to the breastpump; and
   a second coupling part for connection to a milk collection container;
   the breast shield having an electrical resistance heating element for warming the breast shield, wherein the electrical resistance heating element is made of an electrically conductive plastic material and the breast shield is produced in a two-component or multi-component injection-molding operation, thereby connecting the resistance heating element unreleasably to a rest of said breast shield;
   wherein the electrically conductive plastic material comprises a plastic base material and an electrically conductive fibrous or powdery additive; and
   wherein the breast shield funnel has a rigid area and a soft area, and in which the electrical resistance heating element is arranged in the soft area.

2. The breast shield as claimed in claim 1, in which fibers of the additive have a length of 100 to 300 μm.

3. The breast shield as claimed in claim 1, in which the additive is one or more materials from the following group: carbon fibers, copper fibers, iron fibers.

4. The breast shield as claimed in claim 1, in which the additive is powdery and comprised of one or more materials from the following group: iron powder, copper powder, soot.

5. The breast shield as claimed in claim 1, in which the plastic base material is polyamide (PA), polypropylene (PP) or polyethylene (PE).

6. The breast shield as claimed in claim 1, in which the additive is fibrous and is admixed to the plastic base material in a quantity of 10% to 30% (percent by weight).

7. The breast shield as claimed in claim 1, in which the breast shield funnel has the resistance heating element.

8. The breast shield as claimed in claim 7, in which the resistance heating element is embedded in the material of the breast shield funnel.

9. The breast shield as claimed in claim 7, in which the resistance heating element lies on the material of the breast shield funnel.

10. The breast shield as claimed in claim 7, in which the breast shield funnel is made of polypropylene (PP), polyamide (PA) or polyethylene (PE).

11. The breast shield as claimed in claim 1, in which the breast shield funnel has an electrical plug-in connection.

12. The breast shield as claimed in claim 1, in which the first coupling part has an electrical plug-in connection.

13. The breast shield as claimed in claim 12, in which the electrical plug-in connection is arranged adjacent to a suction connection.

14. The breast shield as claimed in claim 1, in which the electrical resistance heating element is arranged in a spiral or circular shape on the breast shield funnel.

15. The breast shield as claimed in claim 1 further comprising a temperature sensor.

* * * * *